US010244938B1

(12) United States Patent
Marino et al.

(10) Patent No.: US 10,244,938 B1
(45) Date of Patent: Apr. 2, 2019

(54) VISION TESTING SYSTEM AND METHOD

(71) Applicant: M&S TECHNOLOGIES, INC., Niles, IL (US)

(72) Inventors: Joseph A. Marino, Park Ridge, IL (US); Kevin A. Butler, Downers Grove, IL (US)

(73) Assignee: M&S TECHNOLOGIES, INC., Niles, IL (US)

( * ) Notice: Subject to any disclaimer, the term of this patent is extended or adjusted under 35 U.S.C. 154(b) by 0 days.

(21) Appl. No.: 15/141,575

(22) Filed: Apr. 28, 2016

Related U.S. Application Data

(60) Provisional application No. 62/153,825, filed on Apr. 28, 2015.

(51) Int. Cl.
*A61B 3/032* (2006.01)
*A61B 3/00* (2006.01)

(52) U.S. Cl.
CPC ............ *A61B 3/032* (2013.01); *A61B 3/0025* (2013.01); *A61B 3/0041* (2013.01)

(58) Field of Classification Search
CPC .......... A61B 3/032; A61B 3/0041; A61B 3/02
USPC .......................................................... 351/239
See application file for complete search history.

(56) References Cited

U.S. PATENT DOCUMENTS

| 1,850,168 | A | * | 3/1932 | Covelle | ..................... | A61B 3/02 |
| | | | | | | 351/222 |
| 5,430,510 | A | * | 7/1995 | Pynson | ................... | A61B 3/028 |
| | | | | | | 351/239 |
| 6,142,631 | A | * | 11/2000 | Murdoch | ................ | A61B 3/032 |
| | | | | | | 351/239 |
| 6,652,101 | B1 | * | 11/2003 | Glaser | .................... | A61B 3/032 |
| | | | | | | 351/239 |
| 2017/0065168 | A1 | * | 3/2017 | Bex | ........................... | A61B 3/08 |

FOREIGN PATENT DOCUMENTS

RU        2158529 C2 * 11/2000

OTHER PUBLICATIONS

VectorVision "Standardized ETDRS-CSV-1000 and ESV-3000" www.vectorvision.com:80/clinical-use-etdrs-acuity, (captured Feb. 19 2015) last viewed Aug. 8, 2017.*
Machine Translation of RU 2158529 obtained from ProQuest.*

* cited by examiner

*Primary Examiner* — Kristina M Deherrera
(74) *Attorney, Agent, or Firm* — Fay Sharpe LLP

(57) ABSTRACT

A method of vision testing includes providing a display, presenting a first chart of optotypes wherein each line progressively decreases in size or in contrast of the optotype relative to a background. The method includes having a patient identify and read the optotypes, noting which line of optotypes at which the patient can correctly identify all of the optotypes in the first chart, confirming that the patient has correctly identified all of the optotypes in the line of the first chart, and then presenting a second chart of optotypes wherein each line of the second chart progressively decreases in one of size or in contrast of the optotype relative to a background. The size or contrast of the noted line of optotypes from the first chart that the patient correctly identified is presented as either a first line of optotypes or a second line of optotypes on the second chart.

18 Claims, 7 Drawing Sheets

VISION TESTING SYSTEM AND METHOD

This application claims the priority benefit of U.S. provisional application Ser. No. 62/153,825, filed Apr. 28, 2015, the entire disclosure of which is expressly incorporated herein by reference.

BACKGROUND

This disclosure relates to vision testing and more particularly to a method of improving the testing protocol to reduce the amount of time of a tester or clinician to complete vision testing with a test subject/patient.

More particularly, this disclosure relates to, for example, standardized visual acuity testing, or low contrast acuity testing, and following an improved method or protocol that provides a reliable, accurate testing of a patient in a reduced amount of time. As will be appreciated, the reduced amount of time that a particular patient requires to complete testing, allows a clinician to handle a greater number of patients in a work day.

A need exists for improved efficiency and a testing without any loss in accuracy, reliability, and flexibility associated with various vision tests.

SUMMARY

A method of vision testing includes providing a display; presenting a clinically accepted first chart of optotypes oriented on a set of lines of the optotypes wherein each line progressively decreases in one of size or in contrast of the optotype relative to a background on the display; having a test subject/patient identify and read the set of lines of optotypes; having a test subject/patient identify and read the set of lines of optotypes; noting which line of optotypes at which the test subject/patient can correctly identify all of the optotypes in the line of the first chart; confirming that the test subject/patient has correctly identified all of the optotypes in the line of the first chart; presenting a clinically accepted second chart of optotypes oriented on a set of lines of optotypes wherein each line of the second chart progressively decreases in one of size or in contrast of the optotype relative to a background on the display, and the size or contrast of the noted line of optotypes from the first chart for which the test subject previously correctly identified all of the optotypes is presented as either a first line of optotypes or a second line of optotypes on the second chart on display.

The method further may include proceeding through the lines of optotypes of the second chart until the patient is no longer able to correctly identify any of the optotypes on a line.

The method further may include noting this line and terminating the test when the patient is no longer able to correctly identify any of the optotypes on the noted line, and recording the number of correct answers read by the patient.

The method includes may include randomizing the optotypes on the second chart.

The method may include each line of the second progressively decreasing in size of the optotype on the display.

The size of the noted line of optotypes from the first chart for which the patient previously correctly identified all of the optotypes, is presented as a first line of optotypes on the second chart, and the method includes prompting the patient to begin review of the lines of optotypes on the second chart on the display starting with the second line of optotypes.

The method may include each line of the second chart progressively decreasing in contrast of the optotype relative to a background on the display, for example, the contrast of the noted line of optotypes from the first chart for which the patient previously correctly identified all of the optotypes, is presented as a first line of optotypes on the second chart, and further comprising prompting the test subject/patient to begin review of the lines of optotypes on the second chart on the display starting with the first line of optotypes.

The method may include using a controller to control first and second displays, or allowing a first device having a first controller operatively associated with the first display device to control an output on a second device having a second controller operatively associated with the second display.

The controller (CPU) includes a storage device for storing test results from the patient.

A primary benefit resides in improved testing time and a system that achieves this improvement.

A further advantage is associated with the ability to use the test method/protocol in connection with various vision tests.

Another benefit is associated with the ability to track the results of patient testing and store the test results electronically and/or provide a display or printout.

Still other benefits and advantages of the present disclosure will become more apparent from reading and understanding the following detailed description.

DETAILED DESCRIPTION

Standardized visual acuity testing quickly measures visual acuity in the ETDRS format. Each presentation may be randomized and is preferably consistent and repeatable. The testing system is calibrated for both distance to a test subject or patient and a pixels/inch so that optotypes precisely follow the well-known standard ANSI Z80.21-2010 and ISO 8596:2009 in regard to size, spacing between optotypes, and spacing between lines. Background luminance can also be set, for example, to 85 $Cd/m^2$ which is typical for standardized ANSI and ISO IOL testing, or alternatively can be set to any other background luminance ranging from and including 80 $Cd/m^2$ up to and including 160 $Cd/m^2$.

Figure 1:
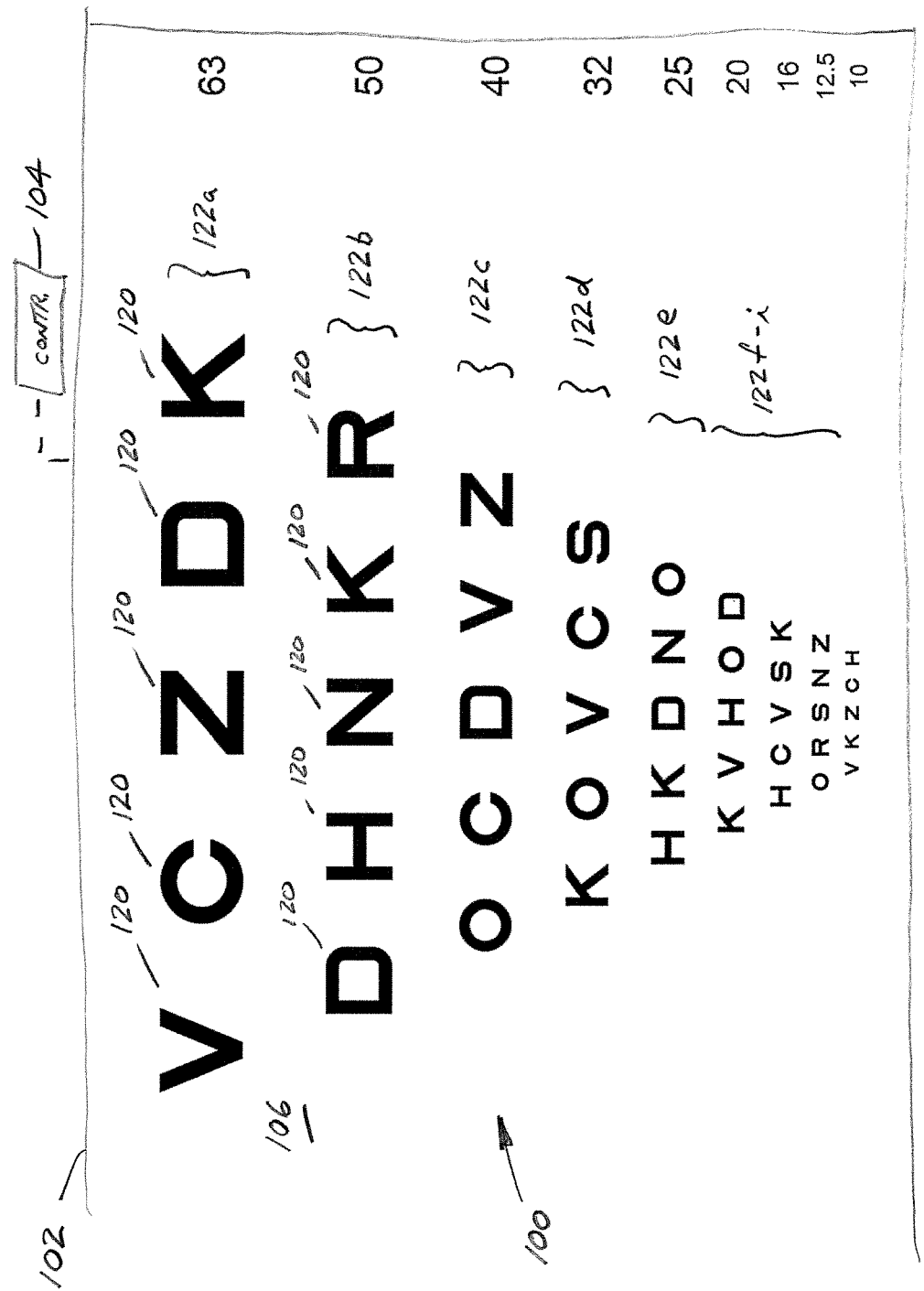
FIG. 1 illustrates an exemplary first chart associated with a first vision test such as a standardized visual acuity test.

For example, and as shown in FIG. 1, a chart such as a descending logMAR chart is illustrated and referred to herein as a first chart 100 that is presented to the patient (not shown) in accordance with a first vision test. The first chart 100 may be displayed on a wide variety of devices 102 such as computers (e.g., desktop, notebook, laptop, networked or stand-alone, etc.), tablets, phones, customized electronic vision testing systems, etc., which electronic devices typically include a controller 104 (associated hardware, firmware, and/or software) for receiving input and providing output, and where part of the output includes a visual electronic display 106 such as a display on a monitor, tablet screen, or computer display screen of the device. The display 106 has a predetermined luminance level (and likewise the testing room, testing lane, etc., would likewise have a predetermined luminance level). It will be recognized that this list of displays 106 is exemplary only and as technology changes and evolves, the particular devices 102 and/or displays 106 associated therewith may be referred to by other nomenclature with similar abilities to display the first chart 100.

In an exemplary embodiment, the first chart 100 of FIG. 1 presents various ones of ten Sloan or twelve British Standard Institute Letters in individual lines of five optotypes 120 (i.e., each line has five optotypes). Thus as shown in FIG. 1, the optotypes 120 are five distinct letters in a line 122 of the chart 100, and six lines 122a-122f of optotypes are shown on the display 106. Here, each successive line 122a-122f of five optotypes is reduced in size relative to the line above it on the first chart 100 according to a well-known format (logarithmic scale) where a specific line is 1.25 times bigger than the line immediately below it. For example in the first chart 100, the upper, first line 122a is representative of eyesight referred to as 20/63 vision, the second line 122b is representative of eyesight referred to as 20/50 vision, the third line 122c is representative of eyesight referred to as 20/40 vision, the fourth line 122d is representative of eyesight referred to as 20/32 vision, the fifth line 122e is representative of eyesight referred to as 20/25 vision, and the sixth line 122f is representative of eyesight referred to as 20/20 vision, etc. Additional lines could be 20/400; 20/320; 20/250; 20/200; 20/163; 20/125; 20/100/20/80; 20/16; 20/12.5; and 20/10, etc.

The patient is exposed to or provided the first chart 100 on a display 106, and the patient is then asked to identify and read the optotypes 120 on a selected line, typically starting with the top line and moving successively downward through the lines of the chart. The clinician (not shown) is noting or monitoring the results provided by the patient, and records the number of correct/incorrect identifications of the optotypes (letters) in a given line. Under prior methods or protocols, the patient is normally asked to read the optotypes line by line, and either the patient will indicate that he/she can no longer read the optotypes on a given line, or the clinician will determine that the patient is unable to read all of the optotypes on a given line. As will be appreciated, different patients with different levels of vision will be able to read the same, more, or less lines of optotypes. Moreover, proceeding line by line through the chart can be time-consuming, tedious, cumbersome but just as importantly is required to provide an accurate assessment of the vision capabilities of the patient.

The method of the present disclosure significantly reduces the time to complete the test in an accurate manner (e.g., from 2-4 minutes according to the prior method to 1-2 minutes or less for the method of the present disclosure). Specifically, the patient is asked to identify on the first chart 100 the lowest line of optotypes 120 that he/she can accurately read. In this instance, the patient is asked to read the smallest line 122a-i where all five optotypes 120 can be correctly read. The clinician will verify that the patient has read all five optotypes of a given line correctly, for example, by reading along with the patient on a second display or monitoring the same display 106 as the patient. The system can be arranged where the chart 100 on the patient's device and the chart on the clinician's device are the same, or the clinician's chart may be modified to provide additional input and/or control of the test protocol as will become more apparent below.

Figure 2:
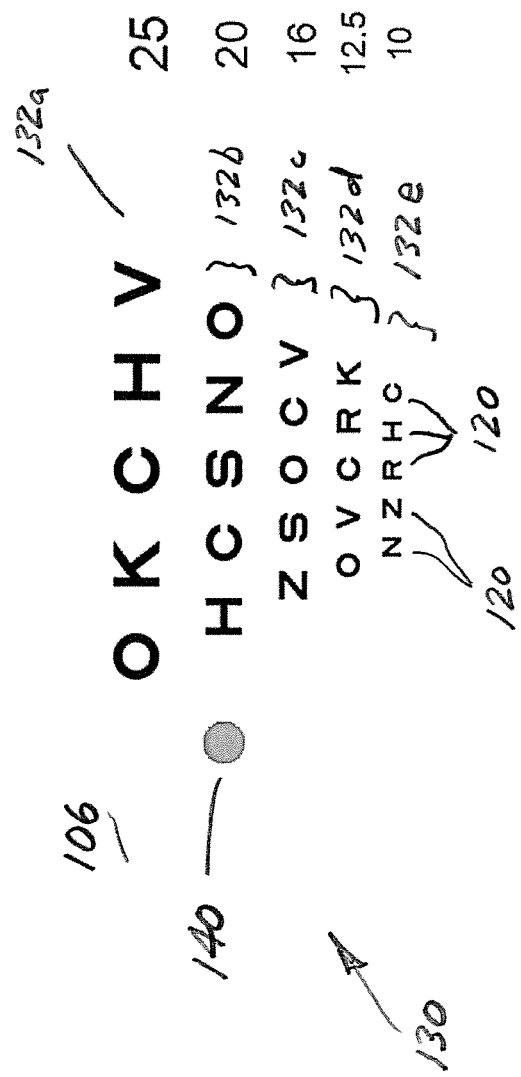
FIG. 2 shows an exemplary second chart associated with the standardized visual acuity test of FIG. 1.

Next, a second chart 130 (descending logMAR chart) (FIG. 2) is presented to the patient on the display 106 once the lowest line of the first chart is identified that the patient can correctly identify all five optotypes. Preferably, a first line 132a of the second chart 130 is the same as the smallest line from the first chart 100 in which the patient was able to accurately identify all five optotypes 120. A second line 132b of the second chart 130 follows the same format as the first chart 100, i.e., each successive line 132a-132e of five optotypes 120 is reduced in size relative to the line above it on the second chart 130 according to a well-known format (logarithmic scale) where a specific line is 1.25 times bigger than the line immediately below it. It is also appreciated that depending on the size of the optotypes 120 which the patient was able to read on the first chart 100 may result in a lesser number of lines being displayed on the second chart 130. The patient is asked to identify all of the optotypes 120 in the line 132b, i.e., the second line on the second chart 130. A pointer 140 may be provided adjacent the second line 132b to direct the patient's attention to reading the optotypes 120 in this line. The clinician notes or inputs the number of correct optotypes 120 identified by the patient. The pointer 140 is then moved to the next, lower line 132c on the second chart 130 where the clinician continues to note and/or input the number of correct optotypes 120 identified by the patient into the system or device. As long as the patient correctly identifies at least one optotype 120 in a line, the test continues to the next lower line. The test continues through descending lines on the second chart 130 until the patient is no longer able to identify any optotypes 120 on a line 132. Again, this information is noted or input by the clinician into the system and the test is finished. The results of the tests input by the clinician are then reported in a standard or conventional manner.

It is also contemplated, although not deemed preferred, that the first line 132a of the second chart 130 need not be the same as the lowermost line from the first chart 100 for which the patient was able to correctly identify all five optotypes. Instead, the second chart 130 may have the first line 132a be the same as the next lower line from the first chart 100 for which the patient was able to correctly identify all five optotypes 120. Likewise, the optotypes 120 from the first chart 100 to the second chart 130 may be randomized (i.e., different) to prevent the potential impact of memorization by the patient.

It will also be appreciated that the number of lines on the charts 100, 130 may vary depending on the type of display 106 presented to the patient. For example, the dimensions of the display 106 may be such that a greater or lesser number of lines can be shown on a given chart 100, 130, e.g., the dimension of a tablet would likely have less lines than a large computer monitor. Likewise, although the example of FIGS. 1 and 2 indicates two charts 100, 130 were generated for use in the test, there may be other tests where more than two charts are generated; however, the same scenario is presented to the patient, the number of correct identifications of optotypes 120 noted and/or recorded by the clinician, and so on, until the test is complete. It is also contemplated that if the display 106 is of a dimension that all of the lines of optotypes 120 of a particular test are able to be displayed on a single chart and the patient is able to read the lowermost line of optotypes on that single chart, then a second chart is not created or generated and the test is over. The present system and method is able to reduce the test time by more quickly advancing or focusing the patient on the line(s) of optotypes 120 that make a difference in the test procedure. Still another variation is that the optotypes 120 of the lowermost line from the first chart 100 for which the patient was able to correctly identify all five optotypes need not be repeated in the first line 132a of the second chart 130, i.e., the optotypes may be randomized.

In still other variations, the patient and the clinician may have the same types of devices or may have different types of devices. The test method or protocol may be run on one device or controller 104 with two displays 106, or each device used by the patient and clinician, respectively, may have its own controller and the two devices are in operative communication whereby the clinician is able to control the test protocol, enter data, etc.

Figure 3:
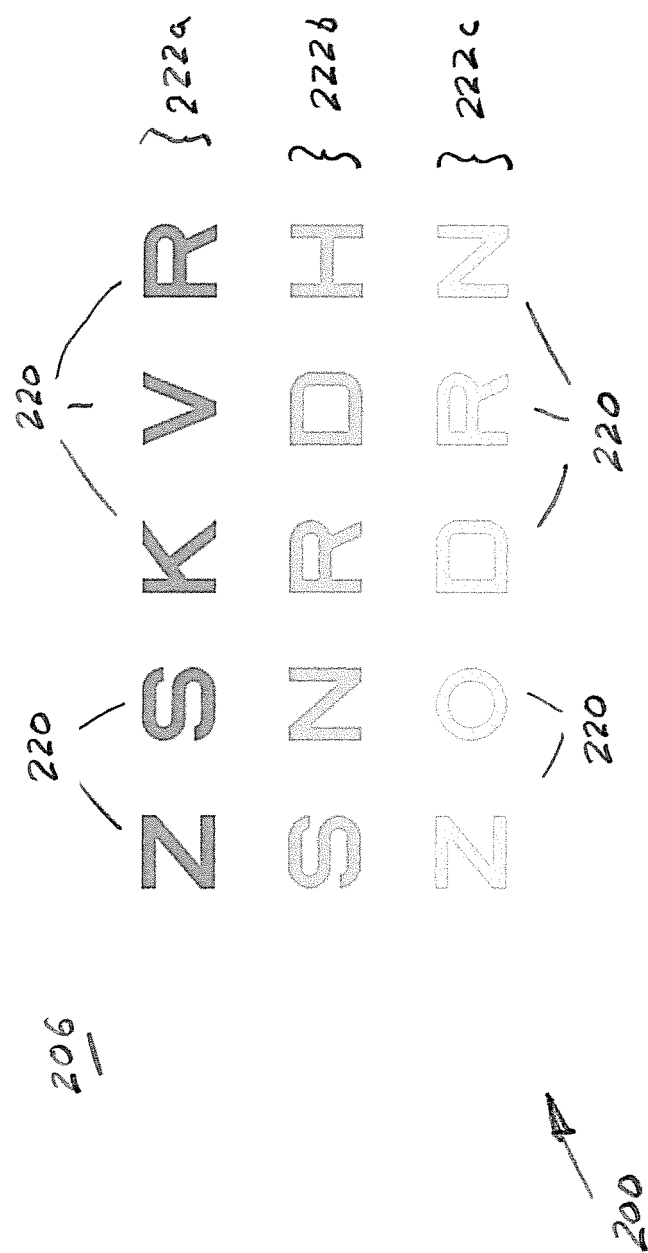
FIG. 3 illustrates an exemplary first chart associated with a second vision test such as a first type of a contrast letter acuity test.
Figure 4:
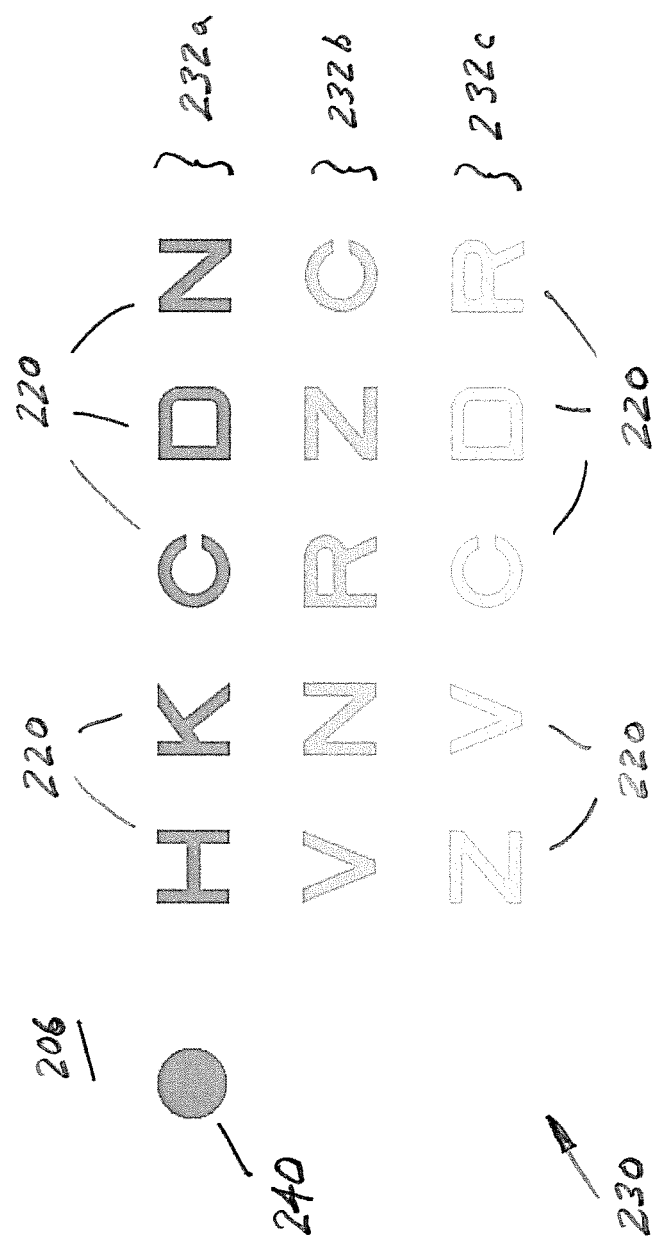
FIG. 4 shows an exemplary second chart associated with the low contrast letter acuity test of FIG. 3.

FIGS. 3 and 4 illustrate a different or second vision test. Like reference numerals in the "200" series will be used to refer to like components in the "100" series of the embodiment of FIGS. 1-2. Specifically, low contrast acuity testing can also take advantage of the present disclosure. Low contrast optotype acuity testing is quickly measured by selecting a clinically accepted chart of optotypes 220 for presentation to the patient, e.g., the low contrast optotype acuity test may select either the Sloan letter set or the twelve British Standard Institute letters for presentation to the patient. The system is calibrated for both distance to the patient and a pixels/inch so that optotypes precisely follow ANSI Z80.21-2010 and ISO-8596:2009 in regard to size, spacing between optotypes, and spacing between lines. Background luminance is set, for example, to 85 $Cd/m^2$ which is typical for standardized ANSI and ISO IOL testing, or alternatively can be set to any other background luminance ranging from and including 80 $Cd/m^2$ up to and including 160 $Cd/m^2$. In the particular low contrast acuity test of FIGS. 3 and 4, the optotypes 220 are maintained at a fixed size and instead the contrast is altered. For example, a three line contrast chart is presented using selectable ten Sloan or twelve British Standard Institute Letters in lines of five optotypes across. The test begins at 10% (−1.0 log) contrast and each line is reduced in −0.1 log steps. The patient is asked to identify the lowermost line where all five optotypes 220 can be read in the first chart 200. The clinician notes or monitors the identification of the five optotypes 220 in the line. If all of the optotypes 220 in the line are correctly identified by the patient, a second chart 230 (FIG. 4) is generated and sets this line (contrast) as the top line on the second chart. It will be appreciated that for purposes of illustration, the actual contrast between the optotypes 220 and the background may not be accurately illustrated because of the need to illustrate optotypes of varying contrast (i.e., if too little contrast, the optotype would not be visible in the drawings). The same or different optotypes 220 can be used in this top or first line 232a of the second chart 230, or the optotypes can be randomized to prevent memorization. In this fixed size, decreasing contrast test of FIGS. 3 and 4, it may be preferable to have the pointer 240 refer to the first line of the second chart 230. The patient is asked to read the line adjacent the pointer 240, and the clinician notes and/or records the number of correct optotypes 220. The pointer 240 then moves to the next line and the test continues with the patient identifying the optotypes 220 and the clinician noting and or recording the number of correct optotypes identified. As long as the patient correctly identifies at least one optotype 220 in a line, the test continues to the next lower line. The test continues until the patient is no longer able to identify any optotypes 220 on a line 232. Again, this is noted and/or recorded by the clinician and the test is finished or complete. Contrast percentage and low contrast data is then presented in a suitable format.

Figure 5:
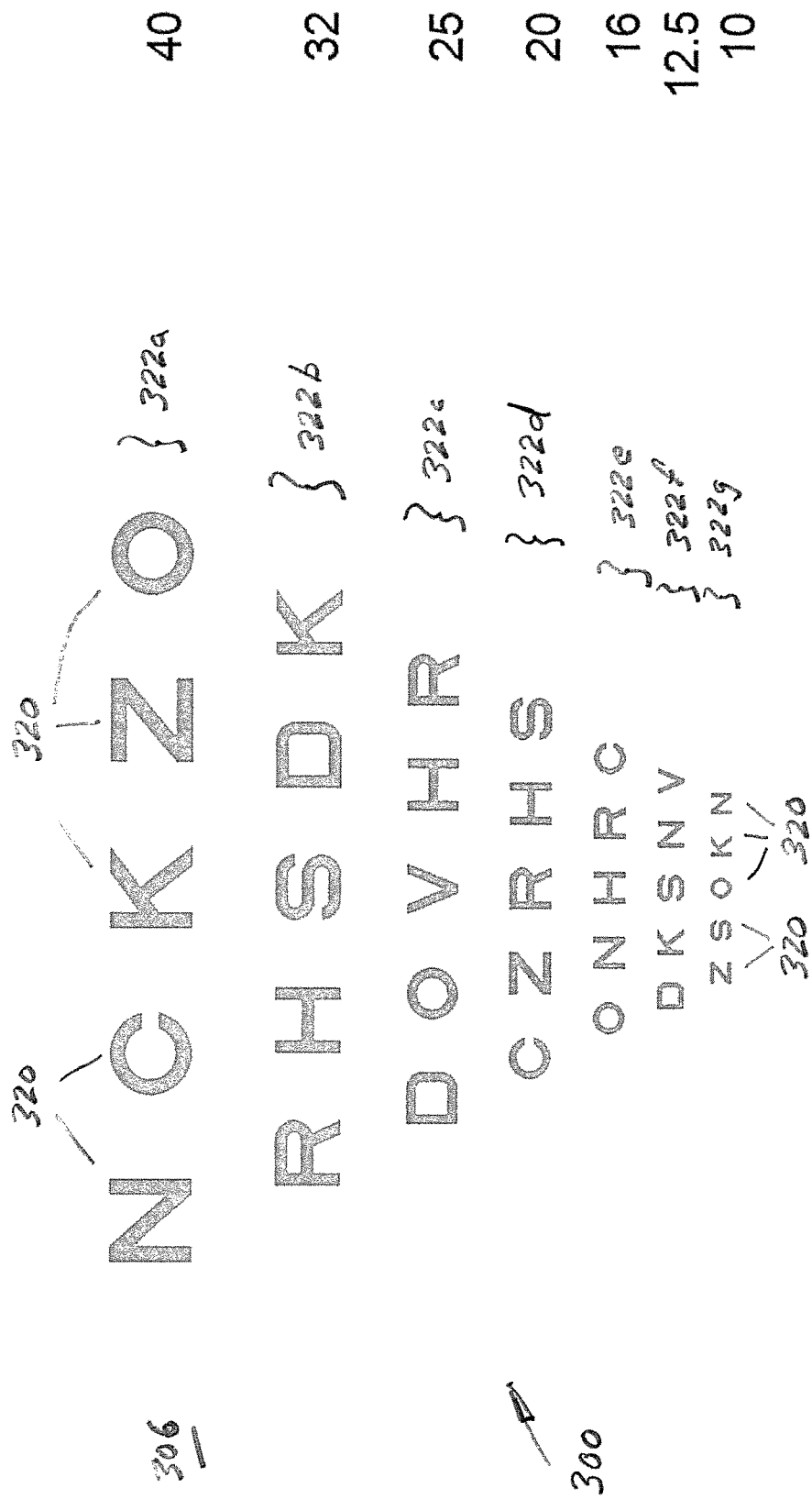
FIG. 5 illustrates an exemplary first chart associated with a third vision test such as a second type of a contrast letter acuity test.
Figure 6:
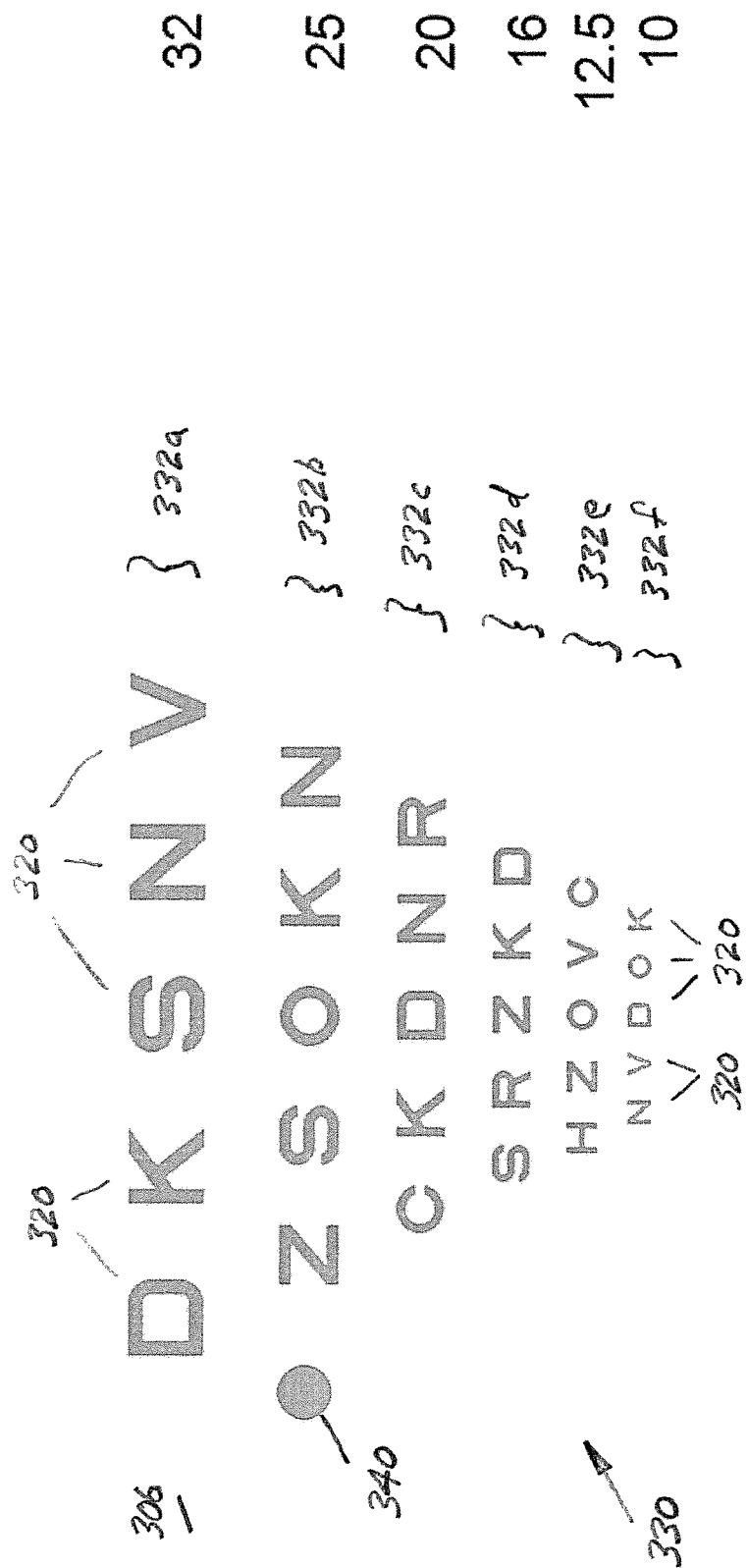
FIG. 6 shows an exemplary second chart associated with the low contrast letter acuity test of FIG. 5.

FIGS. 5 and 6 illustrate a third vision test, which in this instance is a second type of low contrast optotype acuity test. In this test, the contrast of the optotypes 320 is maintained fixed while the size of the optotypes decreases. Once again, the system is calibrated for both distance to subject in a pixels/inch so that the optotypes 320 precisely follow ANSI Z80.21-2010 and ISO-8596:2009 in regard to size, spacing between optotypes, and spacing between lines 332. Background luminance is set, for example, to 85 $Cd/m^2$ which is typical for standardized ANSI and ISO IOL testing, or alternatively can be set to any other background luminance ranging from and including 80 $Cd/m^2$ up to and including 160 $Cd/m^2$. Fix contrast charts are available at 1.2%, 2.5%, 5%, 10%, and 25% contrast levels. These are selectable by the clinician. A descending logMAR first chart 300 (FIG. 5) is presented to the patient with lines 322 of five optotypes 320 across. The patient responds in a similar manner to the above test by identifying the smallest line for which all five optotypes 320 can be read. The clinician notes and/or records the correct identification by the patient of these optotypes 320. If the optotypes 320 in the line are correctly identified by the patient, a second chart is generated and the second chart sets this line (contrast) as the top line on the second chart. The patient can view the second chart 330 on his/her display 306. The same or different optotypes 320 can be used in this top or first line 332a of the second chart 330, or the optotypes can be randomized to prevent memorization. The pointer 340 is positioned adjacent the next smaller line 332b of optotypes 320 and the patient is directed to read this line. The clinician notes and/or inputs the number of correct optotypes 320 into the system, and the pointer 340 is moved to the next line 332c. As long as the patient correctly identifies at least one optotype 320 in a line, the test continues to the next lower line. The test continues until the patient is no longer able to get any correct optotypes 320 on a given line. The testing is complete and the ETDRS-style score and equivalent VA is presented with the contrast tested for recording.

Figure 7:
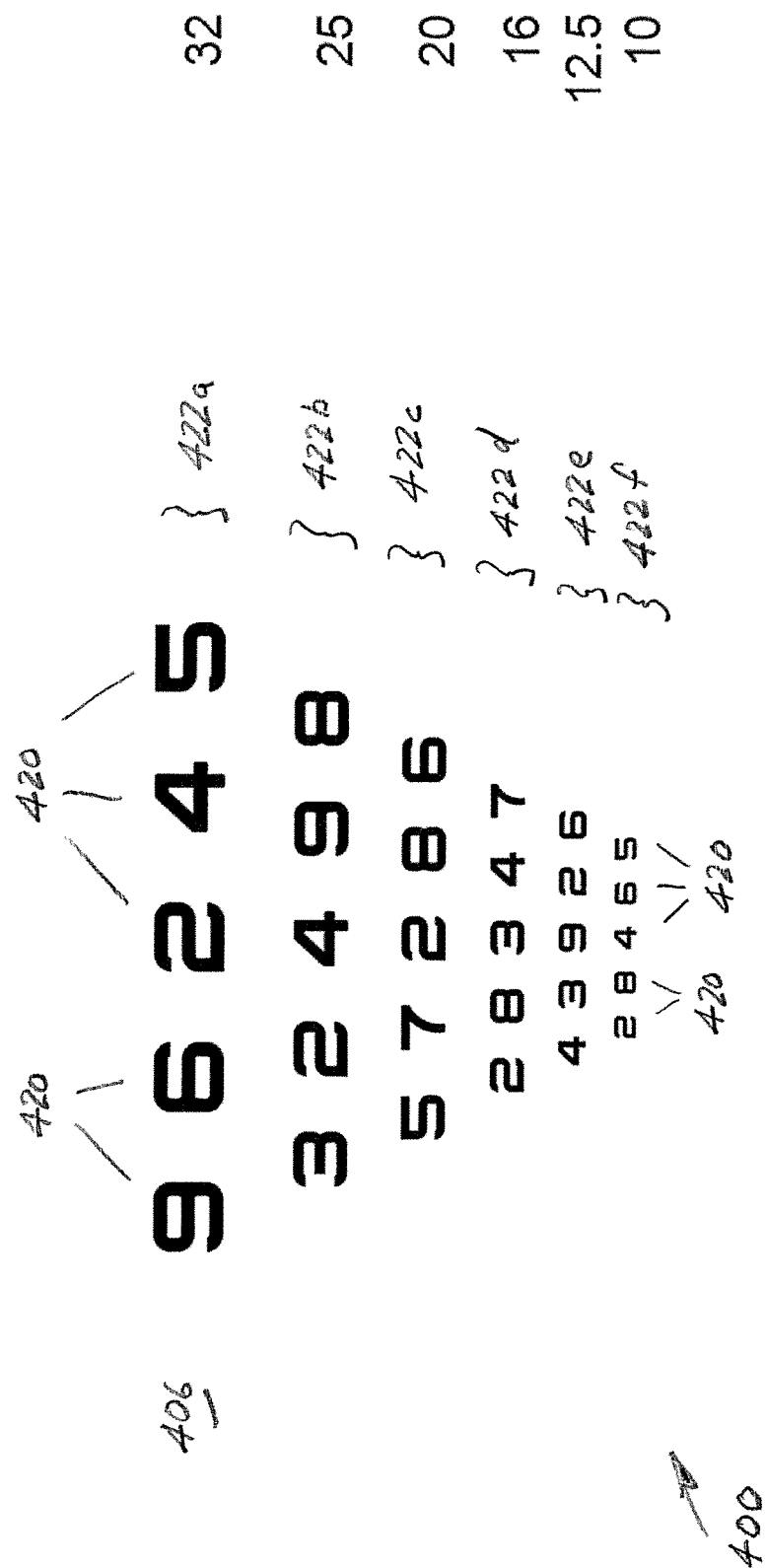
FIG. 7 illustrates another chart that could be used in various vision tests that use of different optotypes.

FIG. 7 merely illustrates that the optotypes 420 may vary without departing from the scope and intent of the present disclosure. That is, examples of different vision tests illustrated and described in connection with FIGS. 1-6 use letters, although one skilled in the art will recognize that optotypes 420 may be letters, numbers, symbols, etc., and in this particular instance are numbers.

Testing can also be conducted at both photopic and mesopic luminance levels.

This written description uses examples to describe the disclosure, including the best mode, and also to enable any person skilled in the art to make and use the disclosure. Other examples that occur to those skilled in the art are intended to be within the scope of the invention if they have structural elements that do not differ from the same concept, or if they include equivalent structural elements with insubstantial differences.

What is claimed is:
1. A method of vision testing comprising:
providing a display including an operatively associated controller configured to present a first chart of optotypes followed by a second chart of optotypes;
presenting to the patient the first chart of optotypes oriented on a set of lines of the optotypes wherein each line progressively decreases in one of size or in contrast of the optotype relative to a background on the display;

having a patient identify and read the set of lines of optotypes;

noting the last line of optotypes at which the patient can correctly identify all of the optotypes in the line of the first chart, wherein the controller receives data regarding the last line of optotypes at which the patient can correctly identify all the optotypes in the line of the first chart;

confirming that the patient has correctly identified all of the optotypes in the line of the first chart; and presenting to the patient the second chart of optotypes oriented on a set of lines of optotypes wherein each line of the second chart progressively decreases in one of size or in contrast of the optotype relative to a background on the display, and the size or contrast of the noted line of optotypes from the first chart for which the patient previously correctly identified all of the optotypes is presented as a first line of optotypes on the second chart on the display, and wherein the first line of optotypes on the second chart randomized with respect to the correctly identified line of optotypes from the first chart.

2. The method of claim 1 further comprising proceeding through the lines of optotypes of the second chart until the patient is no longer able to correctly identify any of the optotypes on a line.

3. The method of claim 2 further comprising noting this line and terminating the test when the patient is no longer able to correctly identify any of the optotypes on the noted line.

4. The method of claim 1 further comprising recording the number of correct answers read by the patient.

5. The method of claim 1 wherein each line of the second chart progressively decreases in size of the optotype on the display.

6. The method of claim 5 wherein the size of the noted line of optotypes from the first chart for which the patient previously correctly identified all of the optotypes, is presented as a first line of optotypes on the second chart, and further comprising prompting the patient to begin review of the lines of optotypes on the second chart on the display starting with the second line of optotypes.

7. The method of claim 1 wherein each line of the second chart progressively decreases in contrast of the optotype relative to a background on the display.

8. The method of claim 7 wherein the contrast of the noted line of optotypes from the first chart for which the patient previously correctly identified all of the optotypes, is presented as a first line of optotypes on the second chart, and further comprising prompting the patient to begin review of the lines of optotypes on the second chart on the display starting with the first line of optotypes.

9. The method of claim 1 wherein the first chart presenting step includes using a LogMAR chart following an ETDRS format of either selectable Sloan or British Standard Institute optotypes.

10. The method of claim 1 further comprising using the controller to control first and second displays.

11. The method of claim 10 further comprising allowing a first device having a first controller operatively associated with the first display device to control an output on a second device having a second controller operatively associated with the second display.

12. The method of claim 1 further comprising using a single controller to control first and second displays.

13. The method of claim 1 wherein the controller includes a storage device for storing test results from the patient.

14. The method of claim 1 further comprising conducting the vision testing under one of photopic or mesopic luminance levels.

15. The method of claim 1 further comprising calibrating both distance to the patient from the display, and pixels/inch so that optotypes follow ANSI Z80.21-2010 and ISO 8596: 2009 with regard to size of optotypes, spacing between optotypes, and spacing between lines of optotypes.

16. The method of claim 1 further comprising selecting a background luminance ranging from and including 80 Cd/m2 up to and including 160 Cd/m2.

17. The method of claim 1 wherein the testing may be one of standardized visual acuity testing, or low contrast acuity testing which can be (i) either fixed size, deceasing contrast optoypes where each line of optotypes is reduced in −0.1 log steps, or (ii) fixed contrast, decreasing size of optotypes where the fixed contrast may be selected from one of 1.2%, 2.5%, 5%, 10%, and 25% contrast levels.

18. A vision system comprising:
a display;
a controller; and
a non transitory storage device;
wherein the controller execute instructions stored in the non-transitory storage device to perform the method comprising:
displaying to the patient a first chart of optotypes oriented on a set of lines of the optotypes wherein each line progressively decreases in one of size or in contrast of the optotype relative to a background on the display;
having a patient identify and read the set of lines of optotypes;
the controller receiving and noting data regarding the last line of optotypes at which the patient can correctly identify all the optotypes in the line of the first chart; and
displaying to the patient a second chart of optotypes oriented on a set of lines of optotypes wherein each line of the second chart progressively decreases in one of size or in contrast of the optotype relative to a background on the display, and the size or contrast of the noted line of optotypes from the first chart for which the patient previously correctly identified all of the optotypes is presented as a first line of optotypes on the second chart on the display, and wherein the first line of optotypes on the second chart is randomized with respect to the correctly identified line of optotypes from the first chart.

* * * * *